US010599122B2

(12) United States Patent
Yoon

(10) Patent No.: US 10,599,122 B2
(45) Date of Patent: Mar. 24, 2020

(54) ELECTRICALLY CONTROLLABLE ROTARY PRESSURE DEVICE AND METHOD FOR CONTROLLING THE SAME

(71) Applicant: RIMSCIENCE CO., LTD., Seoul (KR)

(72) Inventor: Sang Jin Yoon, Seoul (KR)

(73) Assignee: RIMSCIENCE CO., LTD., Seoul (KR)

(*) Notice: Subject to any disclaimer, the term of this patent is extended or adjusted under 35 U.S.C. 154(b) by 97 days.

(21) Appl. No.: 14/787,259

(22) PCT Filed: Apr. 25, 2014

(86) PCT No.: PCT/KR2014/003688
§ 371 (c)(1),
(2) Date: Oct. 26, 2015

(87) PCT Pub. No.: WO2014/175705
PCT Pub. Date: Oct. 30, 2014

(65) Prior Publication Data
US 2016/0085229 A1 Mar. 24, 2016

(30) Foreign Application Priority Data

Apr. 25, 2013 (KR) .................. 10-2013-0046015
Feb. 6, 2014 (KR) .................. 10-2014-0013819

(51) Int. Cl.
G05B 19/18 (2006.01)
B25B 23/14 (2006.01)
(Continued)

(52) U.S. Cl.
CPC ........ G05B 19/182 (2013.01); A61B 17/1626 (2013.01); B23B 41/00 (2013.01);
(Continued)

(58) Field of Classification Search
CPC ....................................................... H02P 3/18
See application file for complete search history.

(56) References Cited

U.S. PATENT DOCUMENTS 3,577,176 A * 5/1971 Kreithen ................... H02P 8/12
318/432
4,251,109 A * 2/1981 Roepke ................. E21C 35/187
299/12
(Continued)

FOREIGN PATENT DOCUMENTS

JP 06-262452 A 9/1994
JP 11-188573 A 7/1999
(Continued)

OTHER PUBLICATIONS

Korean Intellectual Property Office, International Search Report for International Application No. PCT/KR2014/003688, dated Jul. 22, 2014.

Primary Examiner — Mohammad Ali
Assistant Examiner — Vincent W Chang
(74) Attorney, Agent, or Firm — Dinsmore & Shohl LLP; Yongsok Choi, Esq.

(57) ABSTRACT

According to one aspect of the present invention, there is provided an electrically controllable rotary pressure device, comprising: a motor for providing torque to rotary pressure means; a power control unit for supplying power to the motor; a central processing unit for controlling the power control unit; and a rotational speed sensor for measuring a rotational speed of the motor or the rotary pressure means, wherein the central processing unit comprises an abnormality detection unit for receiving the rotational speed from the rotational speed sensor, and wherein the abnormality detection unit transmits a control signal to the central processing unit when abnormality in the rotational speed is detected, so that the central processing unit interrupts the power supply of the power control unit.

14 Claims, 9 Drawing Sheets

(51) Int. Cl.
*B23B 41/00* (2006.01)
*B23P 19/06* (2006.01)
*B25B 21/00* (2006.01)
*B25F 5/00* (2006.01)
*A61B 17/16* (2006.01)

(52) U.S. Cl.
CPC ............ *B23P 19/066* (2013.01); *B25B 21/00* (2013.01); *B25B 23/14* (2013.01); *B25F 5/00* (2013.01); *B23B 2260/122* (2013.01); *B23B 2270/486* (2013.01); *G05B 2219/37133* (2013.01)

(56) References Cited

U.S. PATENT DOCUMENTS 5,801,508 A * 9/1998 Obayashi ............. B60L 15/025
                                                              318/801
2002/0158593 A1* 10/2002 Henderson ................ H02P 3/12
                                                              318/375
2004/0210229 A1* 10/2004 Meller ................. A61B 10/025
                                                              606/80
2006/0081386 A1* 4/2006 Zhang .................. B23D 59/001
                                                              173/2
2008/0066904 A1* 3/2008 Van Hal ................ E21B 36/008
                                                              166/250.1
2012/0261150 A1* 10/2012 Aoki .................... B25D 16/003
                                                              173/104
2013/0189041 A1* 7/2013 Abe ..................... B23B 49/006
                                                              408/5

FOREIGN PATENT DOCUMENTS

JP 2003-001509 A 1/2003
JP 2005-176458 A 6/2005

* cited by examiner

ELECTRICALLY CONTROLLABLE ROTARY PRESSURE DEVICE AND METHOD FOR CONTROLLING THE SAME

FIELD OF THE INVENTION

The present invention relates to an electrically controllable rotary pressure device and a method for controlling the same.

BACKGROUND

A rotary pressure device is being used in a large variety of industry fields, which may directly act as a drill (or drill bit), boring tool, screw or the like, or may be rotated and advanced applying pressure while grasping a component like the above. (A drill, boring tool or the like which may be employed in the rotary pressure device may have a tip as shown in portion A of FIG. 5, so that it may easily pierce into a structure while fragments or the like extracted therefrom may easily get out. Likewise, a screw or the like which may be employed in the rotary pressure device may have a variety of sizes and lengths as shown in FIG. 6, so that it may be appropriately selected and fastened to a structure.)

Particularly, in the medical fields, rotary pressure devices are being widely used for the purpose of boring a hole or fastening a medical screw in a structure within a human body (e.g., bone). For example, the rotary pressure devices are utilized for the purpose of boring a hole in a structure within a human body so that a medicine injection device (not shown) or a test device (not shown) may penetrate into the structure; fixing or reinforcing a broken bone by means of a medical screw in a replantation surgery for fracture repair; or fastening an orthodontic screw within a mouth. A tip of the rotary pressure device may function itself as a drill, boring tool, screw or the like, or the drill, boring tool, screw or the like may be attached to the tip. However, since the rotary pressure devices have been conventionally controlled only by manual sense of an operator or empirical numerical values, they have frequently caused fatal accidents (e.g., fatal medical accidents in which a brain of a patient is damaged) when the operator makes a mistake or is inexperienced. Further, this has led surgeons to perform surgery with excessive caution, so that surgical time tends to be extremely prolonged.

Meanwhile, although the rotary pressure devices are widely used in the fields other than the medical fields, they may also cause serious accidents due to misoperation. For example, when a rotary pressure device and a screw is used to fasten the parts of a pressure vessel, a problem may occur in which the rotary pressure device causes the screw to reach a depth that should not be exceeded and damage the internal structure of the pressure vessel, so that cracks may be created in the pressure vessel to increase the possibility of explosion thereof.

Therefore, the inventor(s) now present an electrically controllable rotary pressure device which is able to prevent medical accidents, has availability in various other industry fields, and also has additional capabilities, as well as a method for controlling the rotary pressure device.

SUMMARY OF THE INVENTION

One object of the present invention is to solve all the above-described problems in prior art.

Another object of the invention is to provide a rotary pressure device which may ensure safety by interrupting the operation thereof when abnormality is detected.

Yet another object of the invention is to provide a rotary pressure device having additional advantageous capabilities.

According to one aspect of the invention to achieve the objects as described above, there is provided an electrically controllable rotary pressure device, comprising: a motor for providing torque to rotary pressure means; a power control unit for supplying power to the motor; a central processing unit for controlling the power control unit; and a rotational speed sensor for measuring a rotational speed of the motor or the rotary pressure means, wherein the central processing unit comprises an abnormality detection unit for receiving the rotational speed from the rotational speed sensor, and wherein the abnormality detection unit transmits a control signal to the central processing unit when abnormality in the rotational speed is detected, so that the central processing unit interrupts the power supply of the power control unit.

According to another aspect of the invention, there is provided a method for controlling a rotary pressure device, wherein the rotary pressure device comprises: a motor for providing torque to rotary pressure means; a power control unit for supplying power to the motor; a central processing unit for controlling the power control unit; and a rotational speed sensor for measuring a rotational speed of the motor or the rotary pressure means, and wherein the method comprises the steps of: detecting abnormality in the rotational speed; and interrupting the power supply of the power control unit.

In addition, there may be further provided other configurations according to the technical idea of the invention.

According to the invention, there may be provided a rotary pressure device which may ensure safety by interrupting the operation thereof when abnormality is detected.

According to the invention, there may be provided a rotary pressure device having additional advantageous capabilities.

DETAILED DESCRIPTION OF THE PREFERRED EMBODIMENTS

Figure 1A:
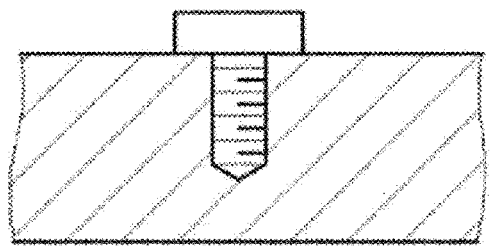
FIG. 1a shows a state in which a screw is fastened to an intended depth.

In the following detailed description of the present invention, references are made to the accompanying drawings that show, by way of illustration, specific embodiments in which the invention may be practiced. These embodiments are described in sufficient detail to enable those skilled in the art to carry out the invention. It is to be understood that the various embodiments of the invention, although different from each other, are not necessarily mutually exclusive. For example, specific shapes, structures and characteristics described herein may be implemented as modified from one embodiment to another without departing from the spirit and scope of the invention. Further, it shall be understood that the locations or arrangements of individual elements within each embodiment may also be modified without departing from the spirit and scope of the invention. Accordingly, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the present invention will be described in detail with reference to the accompanying drawings to enable those skilled in the art to easily implement the invention.

Figure 1B:
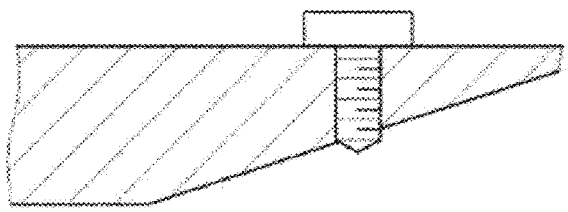
FIG. 1b shows a state in which a screw is deeply fastened beyond an intended depth.

FIGS. 1a and 1b demonstrate the need for the present invention. FIG. 1a shows a state in which a screw is fastened to an intended depth. In the case of FIG. 1a, the screw is well fastened without poking out of a board to which it is fastened. In contrast, FIG. 1b shows a state in which a screw is deeply fastened beyond an intended depth. In the case of FIG. 1b, the screw is excessively fastened so that it pokes out of a board to which it is fastened.

There may be a variety of cases in which a screw fastened by being rotated and pressed by a rotary pressure device is fastened beyond an intended depth. For example, the insertion angle of the screw may be incorrect or the length of the screw may be mistakenly selected. In addition, as in the case of FIG. 1b, the thickness of the structure where the screw is fastened may be thinner than expected, which may cause the screw to undesirably penetrate the structure. In normal cases, it is general that the type or insertion depth of a medical screw is selected to suit to the state of the structure (e.g., bone) to which it will be fastened, on the basis of preliminary MRI or CT scans, for example. However, if there are any errors in scanned images or a surgeon makes a mistake in reading the scanned images, the state of fastening the screw as shown in FIG. 1b may occur frequently, which may cause damage to a human body structure, and even to soft tissues (e.g., cerebrum) within the human body structure. Of course, in the other industry fields, damage to an airtight container other than a human body structure may also be caused in a similar case.

Meanwhile, such damage is also undesirable in the case in which the rotary pressure device is a drill mainly intended for boring or a device for driving the drill.

Figure 2:
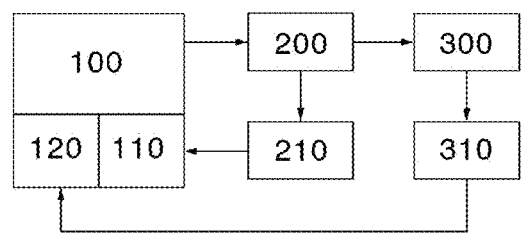
FIG. 2 conceptually shows the control components of a rotary pressure device according to one embodiment of the invention.

FIG. 2 conceptually shows the control components of a rotary pressure device according to one embodiment of the invention. As shown in FIG. 2, the rotary pressure device according to one embodiment of the invention may comprise a central processing unit 100, a power control unit 200, and a motor 300. Further, the rotary pressure device may include at a tip thereof a drill, boring tool, or screw (not shown) which may have threads such that it may be rotated and advanced applying pressure when receiving a rotational torque (and may be commonly referred to as "rotary pressure means"), or may be at least connected or coupled with a component like the above.

First, the central processing unit 100 may be a known microprocessor for electrical control. The central processing unit 100 may be controlled by a user program. The central processing unit 100 may comprise a torque compensation unit 110 for performing torque compensation, and an abnormality detection unit 120 for detecting an abnormal operation of the rotary pressure device. The functions of the central processing unit 100, torque compensation unit 110 and abnormality detection unit 120 will be described in detail later.

Next, the power control unit 200 may be power control means which may supply power to the motor 300 and control the power supply according to a pulse-width modulation (PWM) technique (but not necessarily limited thereto) so that the rotary pressure device may be driven by the motor 300. It may comprise a current sensor 210 to be described later.

Lastly, the motor 300 may be known electromechanical power means. That is, the motor 300 may generate and provide torque when power is supplied from the power control unit 200, so that the rotary pressure device may be rotated while applying pressure. A rotational speed of the motor 300 may be measured by a rotational speed sensor 310 which may be included in or coupled with the motor 300.

Hereinafter, the control of the rotary pressure device configured as above will be discussed in detail.

First, the power control unit 200 may supply power to the motor 300. The motor 300 may be accordingly rotated, and the rotational speed sensor 310 may measure the rotational speed of the motor 300. The measured rotational speed may be transmitted to the abnormality detection unit 120.

Meanwhile, the current sensor 210 may measure a current flowing into the motor 300 as the power control unit 200 supplies power. The measured current may be transmitted to the torque compensation unit 110.

Next, when no signal indicating any particular abnormality is sent from the abnormality detection unit 120, the central processing unit 100 may cause the torque compensation unit 110 to carry out a feedback control such that the current measured by the current sensor 210 may have a predetermined constant value. The predetermined value of the current may be determined based on an output torque value of the rotary pressure device, which may be preset as desired by a user. Thus, when a larger current is measured in the current sensor 210, the torque compensation unit 110 may adjust a control signal from the central processing unit 100 to the power control unit 200 to reduce the pulse width of a power signal supplied by the power control unit 200. When a smaller current is measured in the current sensor 210, the torque compensation unit 110 may adjust the control signal from the central processing unit 100 to the power control unit 200 to increase the pulse width of the power signal supplied by the power control unit 200. Therefore, according to the above configuration of the present invention, the rotary pressure device may be driven while the output torque of the motor 300 is maintained substantially constant.

Figure 3A:
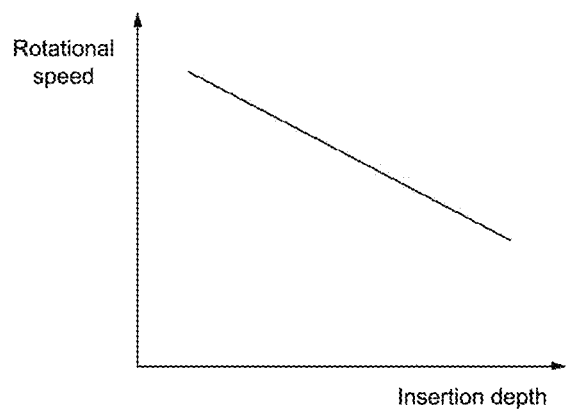
FIG. 3a shows that a rotational speed of a motor 300 may be reduced depending on the depth to which a drill or the like is inserted.

However, since impedance is gradually increased as the drill, boring tool, screw or the like of the rotary pressure device is advanced and inserted to a structure, the rotational speed of the motor 300, i.e., the speed at which the drill or the like is inserted, is gradually reduced. FIG. 3*a* shows that the rotational speed of the motor 300 may be reduced depending on the depth to which the drill or the like is inserted.

Figure 3B:
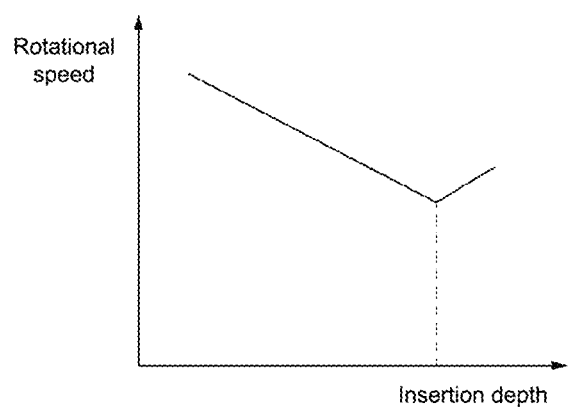
FIG. 3b shows a point at which the rotational speed of the motor may be abruptly increased.
Figure 7:
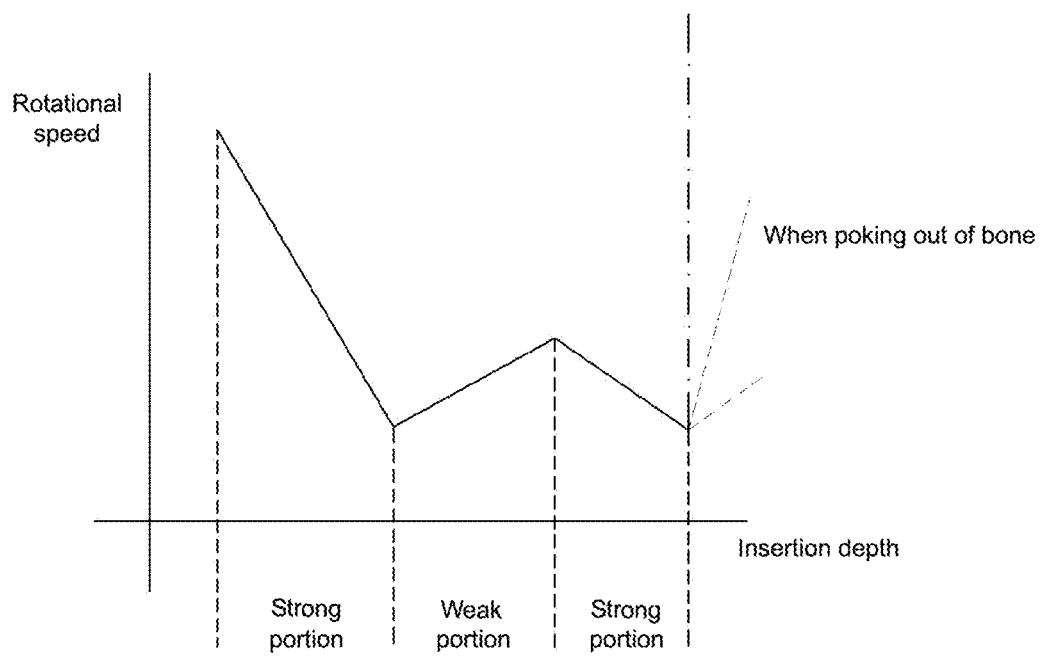
FIG. 7 illustrates a point at which a rotational speed of a motor may be decreased or increased depending on a depth to which a drill or the like is inserted according to various aspects of the present disclosure.

Here, the rotational speed of the motor 300 may be abruptly increased at some point. FIG. 3*b* shows such a point. (Meanwhile, in the case of a bone structure, the point at which the rotational speed is increased may be determined to be a second increase point as shown in FIG. 7, considering the action of the weak portion (e.g., cancellous portion) therein.) That is, as the insertion depth of the drill or the like is increased, the rotational speed of the motor 300 may be abruptly increased while being gradually reduced. According to the present invention, since the rotational speed of the motor 300 measured by the rotational speed sensor 310 is transmitted to the abnormality detection unit 120, the abnormality detection unit 120 may instantly detect such a sudden undesirable situation and then transmit a corresponding control signal to the central processing unit 100. The central processing unit 100 may accordingly transmit a control signal for the interruption of the power supply to the power control unit 200. Consequently, the output torque of the motor 300 may instantly become zero so that the advance of the drill or the like in an undesirable state may be immediately interrupted.

In the above embodiment, it has been basically assumed that the rotational speed of the motor 300 is measured by the rotational speed sensor 310. However, it is also possible to directly measure the rotational speed of the drill, boring tool, screw or the like which is connected to and driven together with the motor 300, rather than the rotational speed of the motor 300. For example, it will be apparent to those skilled in the art to dispose a magnetic or optical mark on the opposite side of the structure like the drill, boring tool, screw or the like, and then measure a cycle in which the mark is magnetically or optically recognized as the drill, boring tool, screw or the like is rotated, thereby measuring the rotational speed of the drill, boring tool, screw or the like. A sensor for carrying out the above type of measurement may also be referred to as a rotational speed sensor, and may perform the same function as the rotational speed sensor 310.

Further, in the above embodiments, it has been basically assumed that the rotational speed of the motor 300 is directly measured. However, it is also possible to measure an acoustic wave generated by the motor 300 or the drill, boring tool, screw or the like, thereby measuring the rotational speed by estimation. In this case, reference may be made to information on one or more of various properties of the acoustic wave, e.g., the maximum amplitude, average amplitude, peak frequency, average frequency, mean value, standard deviation, and effective (root mean square) value of the acoustic wave.

Meanwhile, the above-mentioned rotational speed or data on the properties of the acoustic wave may be displayed to a user via display means (not shown). To this end, known display means may be employed without limitation to display the above physical quantities.

Further, it is also possible to organize the above physical quantities into a database, alone or as being mapped to input values like a torque applied when the corresponding physical quantity appears. In this case, it will be apparent to those skilled in the art that the database (not shown) may be incorporated into or communicate with a computer device (not shown) which may measure or receive the physical quantities or input values.

Figure 4A:
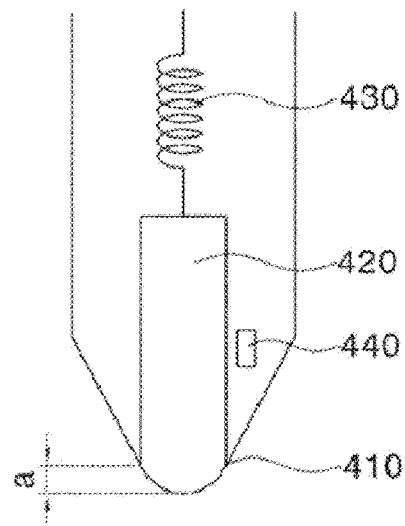
FIG. 4a illustratively shows the internal structure of a drill, boring tool, screw or the like of a rotary pressure device according to one embodiment of the invention.

According to one embodiment of the invention, the collection and detection of a material on or within a structure is possible. This will be discussed with reference to FIG. 4*a*. FIG. 4*a* illustratively shows the internal structure of a drill, boring tool, screw or the like of a rotary pressure device according to one embodiment of the invention.

As shown, the drill or the like 400 which may be included in or attached to the rotary pressure device may comprise a tip opening 410, a tip open/close unit 420, an elastic body 430, and a sensor 440.

First, the tip opening 410 may be an opening which may be disposed at a tip of the drill or the like 400 to open at least a part of the tip. When the rotary pressure device is advanced applying pressure to the structure, a material on or within the structure may flow in through the tip opening 410.

Next, the tip open/close unit 420 may be a component which may be inserted/held in the tip opening 410 to open the tip opening 410 only in some situations. Normally, the tip open/close unit 420 may close the tip opening 410 as shown. While the rotary pressure device is advanced applying pressure, the tip open/close unit 420 may be moved backward by the length of "a" as shown by means of the corresponding pressure to open at least a part of the tip opening 410. By means of the illustrated elastic body 430 which may be disposed at the rear of the tip open/close unit 420 or elsewhere, the tip open/close unit 420 may open the tip opening 410 when pressure is applied and close the tip opening 410 when the applied pressure is released. In this case, the coefficient of elasticity of the elastic body 430 may be determined in consideration of the strength of the intended structure. For example, the coefficient of elasticity may be high if the strength of the intended structure is high, and may be low if the strength is low.

Lastly, the sensor 440 may be a sensor for the existence, concentration, composition or the like of a material. That is, the sensor 440 may function to identify whether a chemical or biological component is present on or within the structure, and to measure a concentration thereof or collect a sample thereof when the component is present. The information collected by the sensor 440 may be transmitted to the central processing unit 100 by means of a data transmission unit (not shown), and may be delivered to a user of the rotary pressure device via display means such as a monitor (not shown) which may be coupled with the central processing unit 100. In connection with the sensor 440 or the data transmission unit, further reference may be made to another patent application of the inventor(s), International Application No. PCT/KR2012/007774.

FIGS. 4*b* to 4*e* further illustratively show the internal structure of a drill, boring tool, screw or the like of a rotary pressure device according to one embodiment of the invention. The improved structure of the drill or the like 400 will be further discussed with reference to the above drawings.

Figure 4B:
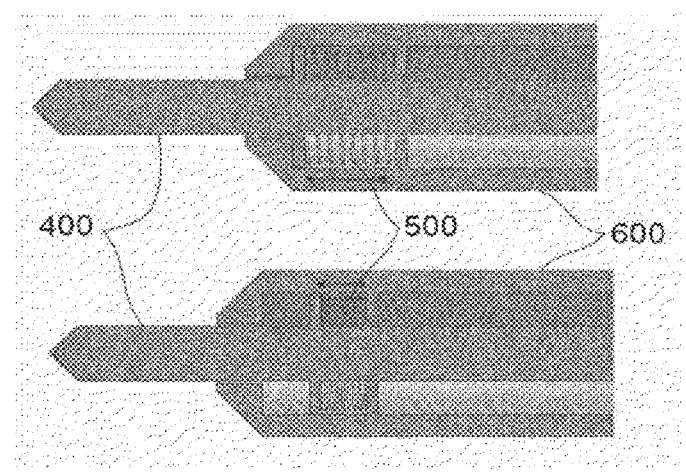
FIGS. 4b to 4e further illustratively show the internal structure of a drill, boring tool, screw or the like of a rotary pressure device according to one embodiment of the invention.

First, FIG. 4*b* shows that the drill or the like 400 according to the present embodiment further comprises another elastic body 500 and an exterior 600, which may be used to measure a force applied thereto in a straight direction. As shown, the force that the rotary pressure device applies to the drill or the like 400 in the straight direction may be simply measured by measuring the length of the elastic body 500. Thus, when the length of the elastic body 500 is undesirably extended abruptly (i.e., when the force applied to the drill or the like 400 in the straight direction by the rotary pressure device is significantly reduced or becomes zero), the information thereon may be considered together with the information obtained as described in the above embodiment (i.e., information on the abrupt increase in the rotational speed), as necessary, thereby interrupting the advance of the drill or the like 400.

Figure 4C:
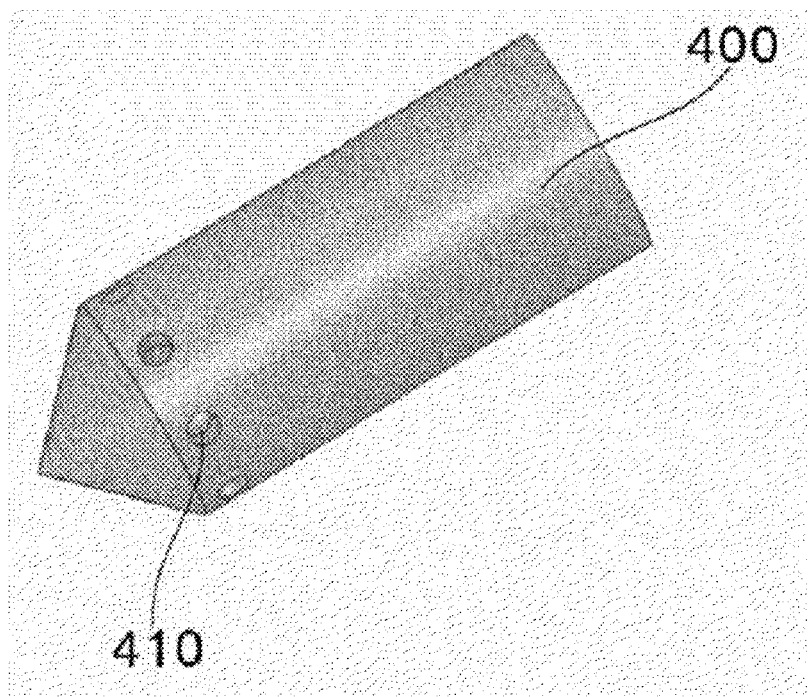
Figure 4D:
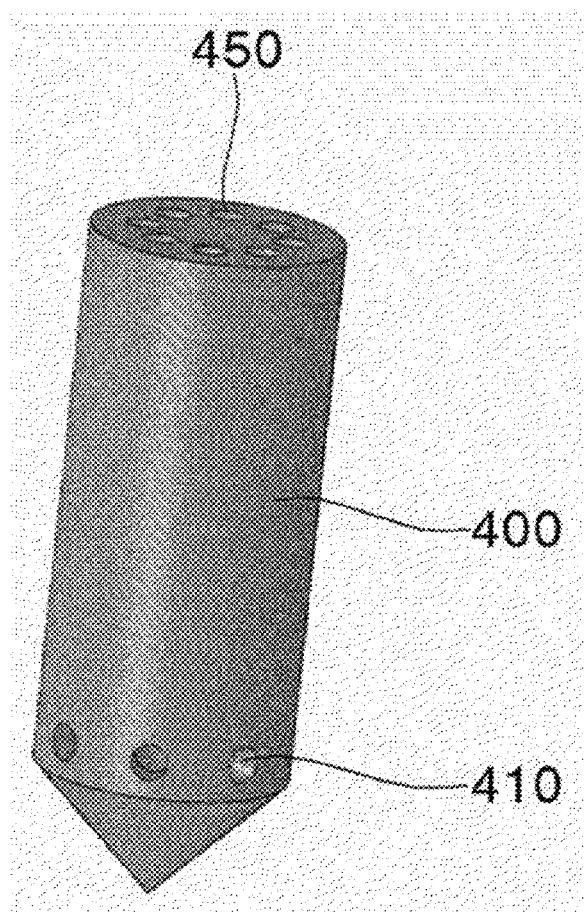
Figure 4E:
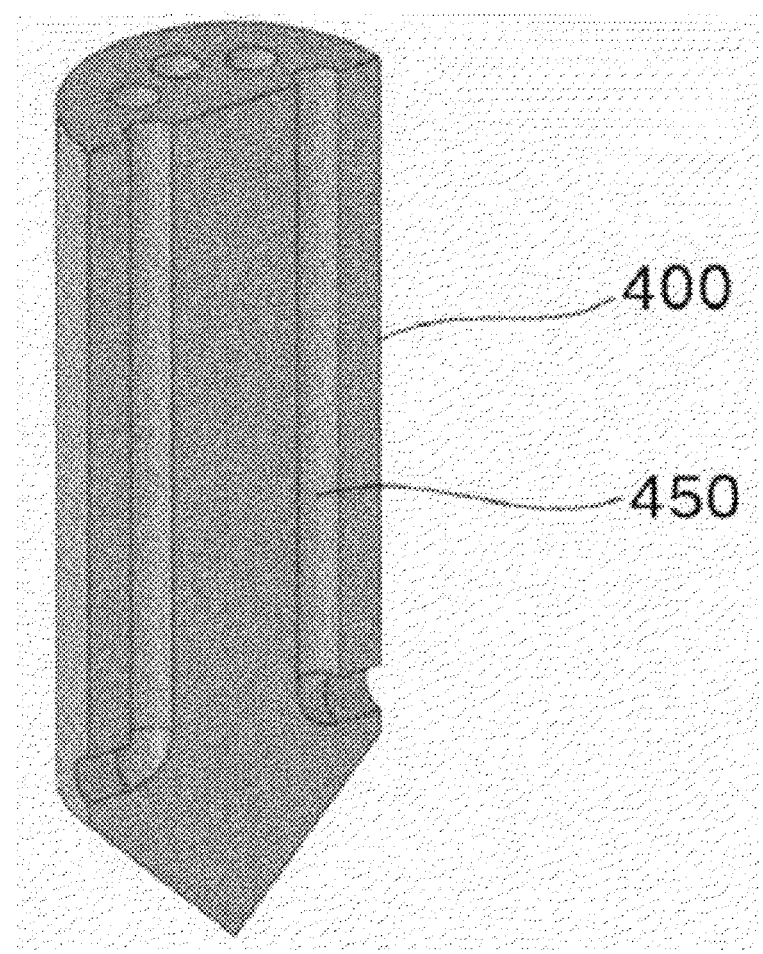
Figure 5:
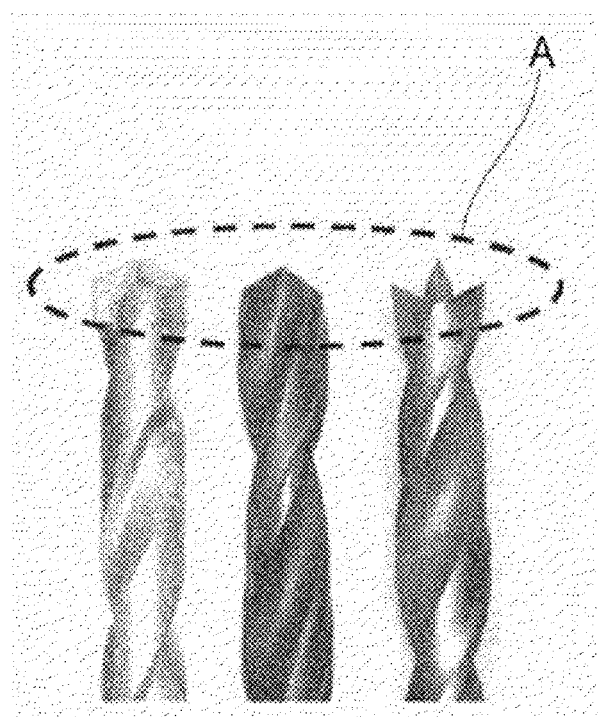
FIG. 5 shows an example of a rotary pressure device illustrating a tip portion according to various aspects of the present disclosure.
Figure 6:
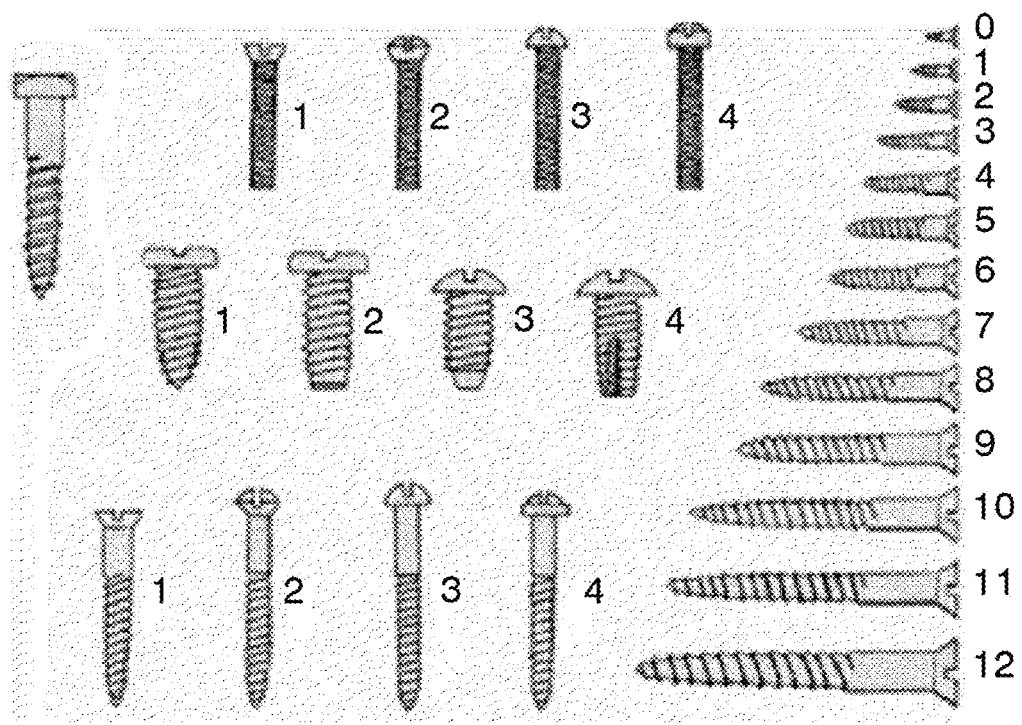
FIG. 6 shows various examples of a screw or the like that may be employed in a rotary pressure device according to various aspects of the present disclosure.

Next, FIGS. 4c to 4e illustratively show the arrangement of the tip openings 410 of the drill or the like 400 according to the present embodiment, and channels 450 extending from each of the tip openings 410. As shown, the tip opening 410 may allow a material on or within a structure to flow in therethrough, and may be disposed in plural to efficiently acquire and detect the material. Further, the above-described sensor 440 may be disposed within the channel 450 to preserve the physical properties of the sensor 440. In this case, the channel 450 may also serve as a passage for delivering the material to the sensor 440 therein. Meanwhile, a suction system (not shown) may be further included in connection with the channels 450 to facilitate the acquisition and detection of the material.

Information on the material detected and identified in the above embodiment may be utilized as basic information to interrupt the advance of the drill or the like 400, as necessary. One example of the above case is when the material to be identified is a fluid of a specific organ within a human body, or a specific material within a structure that needs to be closed.

Although the present invention has been described in terms of specific items such as detailed components as well as the limited embodiments and the drawings, they are only provided to help more general understanding of the invention, and the present invention is not limited to the above embodiments. It will be appreciated by those skilled in the art that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. An electrically controllable rotary pressure device, comprising:
   a rotary pressure means for being inserted to a human body structure to bore a hole therein or to be fastened thereto;
   a motor for generating torque provided to the rotary pressure means;
   a power control unit for supplying power to the motor;
   a central processing unit for controlling the power control unit;
   a rotational speed sensor for measuring a rotational speed of the motor or the rotary pressure means;
   a current sensor for measuring a current flowing into the motor; and
   a torque compensation unit for adjusting the torque by adjusting a control signal from the central processing unit to the power control unit based on the measured current,
   wherein the central processing unit comprises an abnormality detection unit for receiving the rotational speed from the rotational speed sensor,
   wherein when abnormality in the rotational speed is detected by the abnormality detection unit, the power control unit interrupts advance of the rotary pressure means by controlling the power supplied to the motor according to a control signal from the central processing unit for interruption of the power supply so that an output torque of the motor becomes immediately zero upon controlling the power supplied to the motor,
   wherein when abnormality in the rotational speed is not detected by the abnormality detection unit, the central processing unit controls the torque compensation unit so that the measured current has a constant value,
   wherein a dimension or an intended insertion depth of the rotary pressure means is selected according to a state of the human body structure to prevent damage to the human body structure or to human tissue within the human body structure,
   wherein the rotary pressure means comprises a tip opening,
   wherein the rotary pressure means further comprises a sensor for collecting information on a material flowing in through the tip opening, and
   wherein the central processing unit determines whether to control the power control unit so that advance of the rotary pressure means is interrupted, based on the information on the material.

2. An electrically controllable rotary pressure device as claimed in claim 1, wherein the abnormality in the rotational speed is an abrupt increase in the rotational speed.

3. An electrically controllable rotary pressure device as claimed in claim 1, wherein the abnormality in the rotational speed is a secondary abrupt increase in the rotational speed following a primary abrupt increase in the rotational speed.

4. An electrically controllable rotary pressure device as claimed in claim 1, wherein the rotary pressure means further comprises a tip open/close unit capable of being inserted in the tip opening.

5. An electrically controllable rotary pressure device as claimed in claim 4, wherein the tip open/close unit opens the tip opening when the rotary pressure means applies pressure to a structure.

6. An electrically controllable rotary pressure device as claimed in claim 4, wherein the tip open/close unit closes the tip opening by means of an elastic body.

7. An electrically controllable rotary pressure device as claimed in claim 1, wherein the rotary pressure means is a drill, drill bit, boring tool, or screw.

8. An electrically controllable rotary pressure device, comprising:
   a rotary pressure means for being inserted to a structure to bore a hole therein or to be fastened thereto;
   a motor for generating torque provided to the rotary pressure means;
   a power control unit for supplying power to the motor;
   a central processing unit for controlling the power control unit;
   a rotational speed sensor for measuring a rotational speed of the motor or the rotary pressure means;
   a current sensor for measuring a current flowing into the motor; and
   a torque compensation unit for adjusting the torque by adjusting a control signal from the central processing unit to the power control unit based on the measured current,
   wherein the central processing unit comprises an abnormality detection unit for receiving the rotational speed from the rotational speed sensor,
   wherein when abnormality in the rotational speed is detected by the abnormality detection unit, the power control unit interrupts advance of the rotary pressure means by controlling the power supplied to the motor according to a control signal from the central processing unit for interruption of the power supply so that an output torque of the motor becomes immediately zero upon controlling the power supplied to the motor, wherein when abnormality in the rotational speed is not detected by the abnormality detection unit, the central processing unit controls the torque compensation unit so that the measured current has a constant value, and wherein a dimension or an intended insertion depth of the rotary pressure means is selected according to a state of the structure to prevent damage to the structure or to internal structure of the structure, wherein the rotary pressure means comprises a tip opening, wherein the rotary pressure means further comprises a sensor for collecting information on a material flowing in through the tip opening, and wherein the central processing unit determines whether to control the power control unit so that advance of the rotary pressure means is interrupted, based on the information on the material.

9. An electrically controllable rotary pressure device as claimed in claim 8, wherein the abnormality in the rotational speed is an abrupt increase in the rotational speed.

10. An electrically controllable rotary pressure device as claimed in claim 8, wherein the abnormality in the rotational speed is a secondary abrupt increase in the rotational speed following a primary abrupt increase in the rotational speed.

11. An electrically controllable rotary pressure device as claimed in claim 8, wherein the rotary pressure means further comprises a tip open/close unit capable of being inserted in the tip opening.

12. An electrically controllable rotary pressure device as claimed in claim 11, wherein the tip open/close unit opens the tip opening when the rotary pressure means applies pressure to a structure.

13. An electrically controllable rotary pressure device as claimed in claim 11, wherein the tip open/close unit closes the tip opening by means of an elastic body.

14. An electrically controllable rotary pressure device as claimed in claim 8, wherein the rotary pressure means is a drill, drill bit, boring tool, or screw.

\* \* \* \* \*